US007795033B2

(12) United States Patent
McMahon et al.

(10) Patent No.: US 7,795,033 B2
(45) Date of Patent: Sep. 14, 2010

(54) METHODS TO PREDICT THE OUTCOME OF TREATMENT WITH ANTIDEPRESSANT MEDICATION

(75) Inventors: Francis J. McMahon, Bethesda, MD (US); Gonzalo E. Laje, Potomac, MD (US); Silvia Paddock, Solna (SE); Husseini K. Manji, Titusville, NJ (US); A. John Rush, Singapore (SG); Alexander F. Wilson, Phoenix, MD (US)

(73) Assignees: The United States of America as represented by the Department of Health and Human Services, Washington, DC (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/051,494

(22) Filed: Mar. 19, 2008

(65) Prior Publication Data
US 2008/0233657 A1  Sep. 25, 2008

Related U.S. Application Data

(60) Provisional application No. 60/895,649, filed on Mar. 19, 2007.

(51) Int. Cl.
*G01N 33/50* (2006.01)
*C12Q 1/68* (2006.01)

(52) U.S. Cl. ............................. 436/94; 436/63; 435/6; 536/23.1

(58) Field of Classification Search .................... 436/63, 436/94, 173; 435/6; 536/23.1
See application file for complete search history.

(56) References Cited

U.S. PATENT DOCUMENTS

| | | | |
|---|---|---|---|
| 7,083,921 B2 * | 8/2006 | Murphy et al. ................. | 435/6 |
| 2004/0265825 A1 * | 12/2004 | Tartakovsky ................... | 435/6 |
| 2005/0069936 A1 * | 3/2005 | Diamond et al. ............... | 435/6 |
| 2006/0160119 A1 * | 7/2006 | Turner et al. ................... | 435/6 |
| 2007/0003931 A1 * | 1/2007 | Mrazek et al. .................. | 435/6 |
| 2008/0299125 A1 * | 12/2008 | Hinds et al. .............. | 424/139.1 |

OTHER PUBLICATIONS

McMahon, Francis. Neuropsychopharmacology, vol. 31, No. suppl. 1, Dec. 2006, pp. S38-S39.*
Lipsky et al. Neuropsychopharmacology, vol. 31, No. suppl. 1, Dec. 2006, pp. S23-S24.*
McMahon, F.J. Americal Journal of Medical Genetics, vol. 141B, No. 7, Oct. 2006, pp. 689-690.*
Choi et al. Neuropsychobiology, vol. 52, 2005, pp. 155-162.*
Murphy et al. American Journal of Psychiatry, vol. 160:10, Oct. 2003, pp. 1830-1835.*
GenBank Accession No. NM_000621 (Apr. 29, 2008).
GenBank Accession No. NM_000633.2 (Apr. 20, 2008).
GenBank Accession No. NM_000657.2 (Apr. 20, 2008).
GenBank Accession No. NM_000828 (Apr. 2, 2008).
GenBank Accession No. NM_000830 (Feb. 11, 2008).
GenBank Accession No. NM_000833 (Apr. 20, 2008).
GenBank Accession No. NM_014619 (Apr. 6, 2008).
GenBank Accession No. NM_175611 (Feb. 11, 2008).
Mann et al., *Neuropsychopharmacology*, 31, 473-492 (2006).
McMahon et al., *Am. J. Hum. Gen.*, 78, 804-814 (2006).
Rush et al., *Control Clin. Trials*, 25, 119-142 (2004).
Trivedi et al., *Am. J. Psychiatry*, 163 (1), 28-40 (2006).
GeneCard for the IL28RA gene available via url: <genecards.org/cgi-bin/carddisp.pl?gene=Il28ra&snp=284#snp>, printed on Dec. 15, 2009.
GeneCard for the PAPLN gene available via url: <genecards.org/cgi-bin/carddisp.pl?gene=Papln&snp=299#snp>, printed on Dec. 15, 2009.
Halushka et al., *Nature Genetics*, 22, 239-247 (Jul. 1999).
Ioannidis et al., *Nature Genetics*, 29, 306-309 (2001).
Kato et al., *Neuropsychobiology*, 53, 186-195 (2006).
Laje et al., *America Journal of Psychiatry*, 164, 1530-1538 (2007).
Laje et al., *American Journal of Human Genetics*, 141B(7), 724-725, abstract O22.3, available online (Sep. 11, 2006).
Lucentini et al., *The Scientist*, 18, 20 (2004).
Menke e tal., *American Journal of Psychiatry*, 165(7), 917-918 (2008).
Thisted, available online via url: <stat.uchicago.edu/-thisted>, 1-6, (May 25, 1998).
Wacholder et al., *J. Natl. Cancer Institute*, 96(6), 434-442 (2004).

* cited by examiner

*Primary Examiner*—Maureen M Wallenhorst
(74) *Attorney, Agent, or Firm*—Leydig, Voit & Mayer

(57) ABSTRACT

The invention provides a method for determining the outcome of treatment with an antidepressant medication in a patient. In particular, the invention provides a method of screening patients to identify those patients with a decreased risk of non-response to treatment with antidepressant medication by obtaining a sample of genetic material from the patients, and then assaying the sample for the presence of a genotype which is associated with a decreased risk of non-response to treatment with antidepressant medication. The genotype is characterized by a polymorphism in the genes HTR2A, GRIK4, BCL2, and a combination thereof.

25 Claims, No Drawings

SEQUENCE LISTING

<160> NUMBER OF SEQ ID NOS: 39

<210> SEQ ID NO 1
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 1

| | | | | | | |
|---|---|---|---|---|---|---|
| ctcagaggat | gttctccttg | gaggcacagc | tcatcaatct | cttcttgaat | gttgcaaaca | 60 |
| atgggccagg | aacagagagg | gatggaggaa | atgaagagtc | attagccaca | ataagtgtcc | 120 |
| ttatgaacag | ctctgatgtc | atttatctcc | accttccaag | aatcctggat | gggcttgcat | 180 |
| aggcaagtga | caaatattgt | naattaagtc | tttgaagata | atgcaaatg | tcactaagaa | 240 |
| agatttgtgt | tgaatattac | atcaactcag | cgttctttcc | tggccacgat | ggccaatgtg | 300 |
| aggtgacatg | aggttaggac | agtcatgcct | gtgcttggat | gaagcggaac | tctgttctga | 360 |
| gtatgcagaa | gttagattag | agattctcca | aaaacctttt | t | | 401 |

<210> SEQ ID NO 2
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 2

| | | | | | | |
|---|---|---|---|---|---|---|
| atcactacca | catgagttaa | acaaaaaat | ggaataaaaa | acaaaagtgg | tgtctatgta | 60 |
| atcagtgaat | tacttgatag | gacattttaa | ctattttaca | gttcttctta | gcaccagaat | 120 |
| aaactggttc | cayggttaaa | aaaaaaaaag | aaagtaaaat | agatgcaaaa | ataatcactc | 180 |
| ataactgaag | atcatttcac | ntttgaatga | gaatttgtct | ctgaaggcta | acttttctag | 240 |
| gcaaagtcag | gaaacaatgg | cagtggccgg | gtgcggtggc | tcacgcccag | ctactgaggc | 300 |
| agaagaatca | cttgaaccgg | gaggcggagg | tttcagtgag | ctgagatcac | gccattgcac | 360 |
| tccagcctgg | gcaacaagag | caaaactcca | tctcaaaata | a | | 401 |

<210> SEQ ID NO 3
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 3

| | | | | | | |
|---|---|---|---|---|---|---|
| cctgctgctg | ttgtctgacc | ttggacgaat | ctgagttttt | cctccttgaa | gcatataata | 60 |
| agggacttag | ggtcaattat | ctcagcaagg | agtctcttct | atgtctatgc | ttatctgaac | 120 |
| actagagagt | ccagacaagg | ccttgttgaa | ccaaggcact | gcttcaggtg | ccaaggataa | 180 |
| tctggaatgc | agaaccctca | ngttttctta | aattctctag | atggatttca | aataaatgac | 240 |
| aactttatct | tttatatggg | atgagataaa | tcaaattgct | aagtatctaa | gaagtttcta | 300 |
| agatatgagc | ccaggaggca | aatatcaaca | taaatgtttg | tacattggca | ttttcctcac | 360 | agttgggctc tcttctgcag tttcatagct actacaatat t        401

```
<210> SEQ ID NO 4
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is G or T.
```

<400> SEQUENCE: 4
aggaggaact gtcaaacaca taaaaccatc agatctcgtg agaactctca ctatcacgag        60
aacagcatgg gagaaacctc cccatgatcc aatcacctcc caccaggtcc ctgtcccgac        120
atgtggggat tatgaggatt acaattcaag atgagatttg ggtggagaca cagaatgaaa        180
ccatatcaat tggtgtaatt nagtgcttat tagtcatatt aggggctaga attttctgc        240 ccatctaagg aaagatctat ctccaaggaa atatacatat atacaaattt ttcagatttt        300
aggattatca tagacttcct gaagccaatg ttaaaaacct cagaggtagt catagacttt        360
tgtaactacc ttcaaaggaa caaataagca gttttttaaaa a        401

```
<210> SEQ ID NO 5
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.
```

<400> SEQUENCE: 5
aaaattgtaa tttcaaaaaa tgttgatctt ggcattgtgc attaaagact tgcagtaaaa        60
cataactggt ccttagcatt aagttcttaa aagatggttt ctatagccag tcttcccata        120
gatagcatgt aaatggctct aaatgagaaa cgtatagccc ctgcaacaca agcacagata        180
aaaggaggcc tgtccccaca naaagatttc ataggtagga cactgcatga attccaggct        240
ccggatctaa gagccagcct tgagcagcaa tgaagcagca actcrtcaag cagcaacttt        300
tctgaagtga ggaagtttga tccccaagcc tgsatacctg atggcgaaag tgtgctgagg        360
ctacagagca tagaaaaata cagactacag agccaggctg t        401

```
<210> SEQ ID NO 6
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or G.
```

<400> SEQUENCE: 6
gctgatcatg ggaagtaggt ttataaaggg aaaatgaaat ccatagagaa tactaggatc        60
actctctytc caccccgcag gattattctt aatccaatgc ttcaatctcc tgtcattgct        120
gctttactca gaagctccca cacagaaaac acaatgattt gcaattatgt tcctttttcct        180 cagaattaga tggaatcctt ngcaagcagt gaagtgacca cactgataat ggtgagcaag        240
gggaaagcag cagtacattt caggagtact gagtgcagga aaacttgact aatctatgat        300
gtggttaccg aggtgaaaat gtgtcagatc cttgctaact ttgaaagttg gccgcctcat        360

```
ccaagaagct gtctttgacc catgatgcag ttataacagc t                401
```

<210> SEQ ID NO 7
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 7

```
gagggtgtgg ttgaggagcg ccaggtggtg gtggttgtgc cagcctggag gcaggaaaac     60
cagataagag ttaagaggtt gcagttaagt cgttgagatg aaaggaccga agtagggtgg    120
tggtgttaag actggaaaga agtggactgg tttgagaaat tttgaggaag tacaaccaaa    180
agcaattgga gactggttat nggaaggtgc ggaattgggt gaaggcacga tgcctgggta    240
gctggtgctg ctattaacta aacgtaggaa tgttaacagg aagaatctag agggaagag     300
gtgggtttac tttgggtctt cctaaatttg agatgctctg cagatacgtt catggagatg    360
tcaccaggct gttggatata agtaaagcac acccatggag g                        401
```

<210> SEQ ID NO 8
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.

<400> SEQUENCE: 8

```
gatacttcat caggtttcta atgattttgt cagagtgtta atcccatggg tgagtagcag     60
cattttgata ccagcaaaca gattgtgttt cagcccagat aatccaatat ggagatctgc    120
atgagagccg aaaataatta atcacatttt aatggggttg agagaggcta gtcaaggatg    180
ctttacattg gaagtagagc natggggtc agaaagggcg tgagatgtaa gagagaggtt     240
gaacatggga gtagcccata tatatgccag aatggagtgt gcttatggat gtggtatgga    300
agaaagagag gttgtatgtg cagagagcat tgtatggata ttcccttcca tcacagaaac    360
ctttctgcac caggtcttgg gaaaacagag ataaagacca a                        401
```

<210> SEQ ID NO 9
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 9

```
ggaatcaggt cttgtgctct gctcttccta ccatagagca cctgcttctc cagcattatt     60
cacaggattt catcctggct catcactcat tcctcttcca tcattattta agagataatg    120
tctatgacag cacattgtaa actaaagtct aaggtgcta tccatagttg ctgttgttat     180
gactgaggac ttagctgtgt ngagacacca tgtggatgca aaagtgtatg ctatgctctc    240
ccagcctttc aatagcggtg actttaataa tgtcgggaat tcacccagtc tggaggctca    300
ttgtgactta caatccacag ctctgggggtt ttggagaaag gaaagtgcta gtgcgtgtga    360
ttattgcaas ccagagtaaa gatgaggggc tttcagaagg a                        401
```

<210> SEQ ID NO 10
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.

<400> SEQUENCE: 10

| | | | | | |
|---|---|---|---|---|---|
| gaaaactgag | taaatacagg | aaatgagcac | ttttcttgtc | actactattt | gaatgtatta | 60 |
| tttgaataac | caaataataa | atgaggggca | gcatctctgc | ataaaattat | tctagctgat | 120 |
| aaatgaaatc | taaatgattt | atggatccaa | agtctagaca | ttagacattg | agcaccaata | 180 |
| gctgctaata | ctaaaaacag | ngcaaaaagc | aggcattgtg | tgttcctaat | gaagtgcata | 240 |
| gctttggcta | aaagaatwga | acttgagcct | gatcaagcct | cagaatccag | ctgtcaattt | 300 |
| caagaataca | gagacagttc | aacgtgttga | actgcacyga | agtatgcagg | ccacagaatc | 360 |
| cagactggga | gaaattccat | tgggcaaacg | aacaaataaa | t | | 401 |

<210> SEQ ID NO 11
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 11

| | | | | | |
|---|---|---|---|---|---|
| ctcattggct | gagcggcctc | agacaagcaa | tttaagtgac | cttcagtttc | cttttctgta | 60 |
| aaattgggat | catgcgtatc | ccaacaagtc | ctatgtagat | tttaggagac | tgtttccctg | 120 |
| atggtgttga | atttgaatga | gagactacat | accctatttt | ccttttttgg | caaaacagtc | 180 |
| atcattttca | attcaacaaa | natatgagta | gttattctac | atccagccca | atcttaggtg | 240 |
| ctgtggggga | gacaacaggt | aagagatgat | gccggcccct | tgtctttcaaa | attagaggct | 300 |
| tgagaataac | gaagacacca | gaatctgttt | tccttttttg | ttttgttktt | taaacagctg | 360 |
| tgctgagatg | aatttacata | acatatratg | cacccattta | a | | 401 |

<210> SEQ ID NO 12
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or C.

<400> SEQUENCE: 12

| | | | | | |
|---|---|---|---|---|---|
| tggggaagtg | ggggtgttgc | tcctcaggaa | attccaggga | tttggatttt | attgttcaag | 60 |
| gaaagatagg | aggcaaaacc | ttggaactgt | gttaggcgag | agttagaatt | gagaacccca | 120 |
| cataaaggca | gtgctttcaa | ggccacgccc | ttggtgaaat | gaggactgta | aaacagcyga | 180 |
| ctcataggta | gaggggataa | nctgggctct | gagttagaaa | aaattgtccc | ctgggacttt | 240 |
| ataaccacag | actactctca | aagggtttga | agtttaaact | tatacccctct | gctggtccaa | 300 |
| gaattaccaa | gttaaaacat | ttgtatagaa | agtggtcaca | ggctggtaat | gctcctgaag | 360 |
| tttctgacag | aagcaaaaca | aaaccctcaa | gtgaacaaac | c | | 401 |

<210> SEQ ID NO 13
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is G or T.

<400> SEQUENCE: 13

```
tgccctctcg gggtcgccac ggccacactg attggggtga gctggaaggc gctgcagggg    60
ggaggagtcc cctctagcat tgacacaagc atgggacaag aatatggaga ggagtttggg   120
gggcggagaa gggcacaatc aaggggctcc ccttttcttg gcatgagcca tagaactcag   180
aactgggcac agggtgaagt ncttggggct catggggaga aaggctcaat ggaaatgcaa   240
gggatcccgg cttcctgggc atgccggagg catcttgaat ccacctgggt tggaagagtc   300
agtgtgcact gaggcccccat ggatggaaag agcgggaagc cccgggtctc tgaacgcatc   360
tccccatctc agccctgcct ttgctgtggc cccagacctc c                       401
```

<210> SEQ ID NO 14
<211> LENGTH: 402
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 14

```
aaagacagaa gactcttccc attatcgctt cagccttttc tctgtgcttc taggtaacac    60
tgctggcttt agtcttctgg cttttggagg cttagttctc actgaatggt ctttgatgta   120
atttatttct aaggtgaatg tatatgtaga tgcatgaggt aaaaggtgtt tttccccatt   180
cccagatgag tgataagatg nctgagctga cttcttaaaa cctattgcca ctctacctcc   240
atcagctgca aaagaaagtt cctctagcat tagtaagtga ctagaaaaaa tgtcgtgccg   300
atagtgtgat agaacacagc cagaaagaac aagagcggtg caggccggct ttcacttaca   360
ctccattctt atcatcaata gcctcatcat tttaagcaga ay                     402
```

<210> SEQ ID NO 15
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or T.

<400> SEQUENCE: 15

```
gtgccctcca gaaatgagca ttcctcgggc tgttgaatgg ctaagcagta ttccattctg    60
aaagacagta ataccccaca cttggcctcc cttgggctgg tgccacaggg gctcaaaatg   120
tctcaaccca taaagacttt ctctccccat ttcctctctc catctcaacc ttggagggtt   180
tctgttccta atgctattct ncatggcagc tgggatcagt gcaagctcca gggccaagtt   240
ctacaagcct ccttcctgct gacgtggagg aaggagccga gggagagatc tctctggccc   300
cagcccctgc ccattcatgc atcagaaact tgctgtctct attctaagct atttacctcc   360
cagtcgttgc tattccaaaa gagagccaga ggggaggaaa a                       401
```

<210> SEQ ID NO 16
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or T.

<400> SEQUENCE: 16

```
actttagccg cataataacc ctgtgaagtg agtctctgat ttcatatttg agtcatgcaa        60
acttagagat gttctatgat tttaaaaaa ttaatagctg agaaaggatt caaatttagg       120
tcttgtgagt ctccaagttt agtgcttgtt ccagtacttt gcacagttcc taggatgaat       180
gatggaaatt ttcatatagg ntgtggagat tcacagggat ggtatctgcc ttggaagttg       240
agtggaagtt gggggtatga caataccctag gcttttgtgt ggacttaact cgtattcttt       300
aggacaaagt aactatacac tatgactgtc tctgatggga ttgaaccatt ttcccatcca       360
tttatccacc catgcaccca gctagtcatc cyaagattaa t                           401
```

<210> SEQ ID NO 17
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or C.

<400> SEQUENCE: 17

```
agctggtgtg tgatggaaga aggatgtaag tggaggtccg cctgccccg aaggctgtgt         60
tcaccaccac tacatcatgt ggaacaactg gcagcgggaa ggaggtattc tagaggagaa       120
atttagggag ttcctcctcc taccttaga aggtgtctg cttcctttcc tctcactgga         180
tgcaattgat tctacctgaa nccagctaat tagaactcag ggtataggca tttattgcat       240
ctcccagacc ttgtaatttt taactttttt ttagagacat ggtctcactc tgttaccagg       300
ctggagtgca ggcacaatca tatcccacta cagcctcaaa ttcctgggct taagggtct        360
tcctgcctca acctcccaag tagctgggga cacaagtgca c                           401
```

<210> SEQ ID NO 18
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or G.

<400> SEQUENCE: 18

```
atcaaactca aagtcaagag gtgaggaact gtatcctggt tcttaagtgg cagggaccac        60
agaatcacgt gacagtgaca tgtttccagt aagagatgaa gaattgggcc agttgtgcaa       120
tcatgcaatc tactgcaaaa ggttttttgt tttttttttt cactttrttg cccgggtatt       180
ccctaaaaca cccagagact ntagctctta aatataaggc tgattaaagc tgatcgatgc       240
cacctgacta taatactgtc acttgagtga aggtgccaat gctacgcagc aaatgtagga       300
gagatgctgt agattaactg tatgttttta gaagctatgg aggcccagcc cctcctacaa       360
gtcagggctg aacctagtgg tctagtaaga tggggaggcc t                           401
```

<210> SEQ ID NO 19

<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 19

| | | | | |
|---|---|---|---|---|
| ctcgtaataa aaatttccct caatgttctt tgaggcatcc acttaaataa ctcaaaaatg | 60 |
| ttttttgcat tctttaagag gtttttatra gccagacaac cttaataacc atggcctcaa | 120 |
| tcacagacag taaaaatatg ctttgcattt ctcttctaac cctaataccct aagccagctc | 180 |
| ctggtaaaat gttatccgaa ncttttact caattcatga caggttttg ggatatattc | 240 |
| tactttccag gcactgagtt aaattctgga gaccagaaga ccaagacgtt gtccctacac | 300 |
| tgacatttta tctaatagtc ctgttttcag attccttgcc ctaagctctt cctatttttt | 360 |
| gatttctctc ctccagttct cattccatat cagagggctc c | 401 |

<210> SEQ ID NO 20
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.

<400> SEQUENCE: 20

| | | | | |
|---|---|---|---|---|
| aaaataaact tagttgaaac agattgtcag gtaatatcta tgaccactct tctacccaaa | 60 |
| atagggaaaa gaggtttcaa tgagaccttc ctctgtgtgt gtcaagtcac agtcagagat | 120 |
| tcatttgggc gatttcaatg taaaatgaag tgacatgcct aaaatcaaat gcttgagagt | 180 |
| tcaagtaaag cagaaagatt ngaatttctt aacataatgg ttttgggaa aattcacaaa | 240 |
| aagctatcta tagtgataaa aaatattttt aaaaggtaat gtgtagatga tttctcatga | 300 |
| aagctcttgg tttgggcagt ccagatatac tgagttcaaa tgcaagctct ttttcttggg | 360 |
| taagttactt aatgtctcca atagtaaatt tccccatcta t | 401 |

<210> SEQ ID NO 21
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.

<400> SEQUENCE: 21

| | | | | |
|---|---|---|---|---|
| agagtcaaga aatagaaaag caaaggagga tggagcctaa cactcctgtc tgtcttccca | 60 |
| ttagaggaac atatttaggg accaagcata gctccaccct gtccatctca gagcgggtcc | 120 |
| aagtgttcat gttcctaaac tgccacttgt catagctctt ttaccttatc agaatctgaa | 180 |
| tttttaaaaa aatgagtcca nattccttca tgacagggta aggttgaaga aatgactgag | 240 |
| gcagccattt caatgtcctt tcttgttact atgtgtgcag gtcttaycaa catgcaccaa | 300 |
| cacttccaca tacatcatct gattatttga tcttctcatt attcctgtga aatactttat | 360 |
| aggtaaagaa tcaactgaag ctcagaaagt ttagaatctc a | 401 |

<210> SEQ ID NO 22
<211> LENGTH: 401

<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 22

| | | | | | | |
|---|---|---|---|---|---|---|
| cccagcttcc | agatcatagg | tgcttcatga | atcactttca | ttaaacccct | ctatggtatc | 60 |
| ttgcctatga | ttgtagaatt | ccagagctaa | agctcgtttt | atgcaaaatc | ttcacttact | 120 |
| gtgcatttct | ctgtggccta | aaaagggac | aaaatgactc | aaccaaggcc | gcaaaacttg | 180 |
| atagtggctt | aaagactaaa | nttggtttct | tgactcccaa | tcaaagatat | rtcgctattt | 240 |
| ttagatggaa | ttatgagttg | agaaattatg | ggttaaaaga | gagaaacgag | tgacagaaga | 300 |
| cagaaaagta | aaaacacaaa | ttaataaaat | tttgttttgg | aacaaattag | agcgagaaaa | 360 |
| aaattaaagt | gcctaagggc | tatgccattt | tgttaaatac | t | | 401 |

<210> SEQ ID NO 23
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 23

| | | | | | | |
|---|---|---|---|---|---|---|
| tctgatttaa | ctttcgaaag | tgcagtgtta | gctttcaaag | aggtccagga | tgggttccca | 60 |
| aggctgttgg | gtgctggatt | cagcccttgt | tgggaattgg | ggcaaatttc | caggccaaat | 120 |
| agaggaaaga | atagaacagg | tgtactgtta | gtgattgctt | tgctcaaaat | ctttaggtta | 180 |
| tagaagactt | gggagccctg | ngggtaaac | tgattttccc | agagtcactg | aagtcttgtt | 240 |
| acttgcagga | aatccaaagt | tacgggagac | tgaggttggg | caaatgaggc | tatattgtg | 300 |
| agccaggtga | aaccgcaaaa | gcctttgacg | ttggaaaatt | tgacagagaa | gggctcatgt | 360 |
| ttcaaaataa | tttctgatta | aagtatatca | ttttgcatc | t | | 401 |

<210> SEQ ID NO 24
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 24

| | | | | | | |
|---|---|---|---|---|---|---|
| gcactccagc | ctgggcaaca | agagcgaaac | tccaactcaa | aaaaaaaaa | gaaaaaagaa | 60 |
| gttattctta | gaacacctca | catatgattt | tatttataaa | taattgattt | gcctacaaat | 120 |
| ttaaggaatt | agagaatcca | tgtgaccttc | tccagtagtg | ctatgatcct | gggaacctac | 180 |
| caagtgtaaa | gtggatgttg | natctatact | gtggggcact | atattttact | gattctgaaa | 240 |
| ttagtacacc | ctgactgata | ctttgaggct | acttactggg | aaaaaagacc | atttcatacc | 300 |
| agtcttgtcc | tagaagtagg | gtaataaatg | attctggttt | tcacctggga | ctgagagtat | 360 |
| ctcccctgga | catgggacct | tccatttaa | aatctagata | a | | 401 |

<210> SEQ ID NO 25
<211> LENGTH: 401
<212> TYPE: DNA

<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 25

| | | |
|---|---|---|
| cattctttac actcaatatc aaaaaaaatg ataaattaca gtttcttttt ttctctgtac | 60 |
| tcactttttt ctaccottca tatctcccac ctcggttctt tgaccagaac cttacttaaa | 120 |
| tattcagaac tatgcccagg aaaccaatat ttagatattc caggccaggc atattctttt | 180 |
| tagctactgt tgaaacttaa ngagaattca gcaccaacat atactggtgg agctgagtgc | 240 |
| aatacacttt cttgaatact tagactagat tcttctataa gctcctttgt aaccaaggta | 300 |
| cacaattttt cttttgggaa gactcccact tgccttctct gttgcacttc tgaaaaacgc | 360 |
| tatgtatgaa gatctgcact ttaaaagcat tgtgtttccc c | 401 |

<210> SEQ ID NO 26
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or C.

<400> SEQUENCE: 26

| | | |
|---|---|---|
| tacaaggtaa gttgagtcag aacaatatat tcctttgaga ggaataagat agaaaaccat | 60 |
| tattttcctg tgttttttttt gtttgttttt tccatcatta aatgagatgg attctctgcc | 120 |
| acaatgaaac attgtctgaa attccttttg ggaagaagag ggtaaattta atactttcac | 180 |
| taatctctca gcacaggctt narctawaga cagatggaat cagtaggcag cagtggaatt | 240 |
| gcctcccttt aaggttctta cccacaacaa tggcttgatt tccaccatgt tacactgagt | 300 |
| tgattcggat agctccctgt tccatggaaa cagtgattga aaagcaggtt aggaagtatc | 360 |
| cttggaacct aaaaaaaaag tcaatcagtg agacctagag c | 401 |

<210> SEQ ID NO 27
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 27

| | | |
|---|---|---|
| tggtgaacgt ccatcagtta tttgttgact gaagaaatgt ataatctaat tgacacactg | 60 |
| cattctccac ttataagyta ttatgataca acccttcatc cacactgtgy tgtaatgatt | 120 |
| tatagcagtg aaatatgatc gacagtgcta actctcacat cctcattctt atagcacttg | 180 |
| ctcatgggtc tcatccacca nctgcatccc ttggcccttc actcatctct tcactgartc | 240 |
| cattgtattc ttactttgtt ccttattcga cctaggccct atccccttc acgtcaagtt | 300 |
| tcctctcacc aattcactga gccttgctga ccttggcctt ctatcacata ttccctgcag | 360 |
| tttcccaaac ctaaataatt gaatccatcc tgcacatgag t | 401 |

<210> SEQ ID NO 28
<211> LENGTH: 401
<212> TYPE: DNA
<213> ORGANISM: Homo sapiens

```
<220> FEATURE:
<221> NAME/KEY: misc_feature
<222> LOCATION: (201)..(201)
<223> OTHER INFORMATION: "n" is C or T.

<400> SEQUENCE: 28
ctcgtaataa aaatttccct caatgttctt tgaggcatcc acttaaataa ctcaaaaatg      60
ttttttgcat tctttaagag gtttttatra gccagacaac cttaataacc atggcctcaa     120
tcacagacag taaaaatatg ctttgcattt ctcttctaac cctaatacct aagccagctc    180
ctggtaaaat gttatccgaa ncttttract caattcatga caggttttg ggatatattc     240 tactttccag gcactgagtt aaattctgga gaccagaaga ccaagacgtt gtccctacac    300
tgacatttta tctaatagtc ctgttttcag attccttgcc ctaagctctt cctatttttt    360
gatttctctc ctccagttct cattccatat cagagggctc c                         401

<210> SEQ ID NO 29
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.

<400> SEQUENCE: 29
gtagtaaaga aatattgaag ggaagtgcag aagcattgct cctggctctc acaggtggac     60
aacatgcagg tggacaatat aacccagttt gctgtatttg tcagggggag ggattcttat   120
tctgctctac ttcctccctc ttagtcccca ttcgaagcag gattaactgt cccctggcat    180
atggtggttc agggtcagcc naagagcatt cttttcccta aggccctctc agtaactatt    240
gggaaaagcc atcttatata gccaatttag ggctagaaag aaaagaattt tacagagttt    300
gcagttgaat gacagaagac agaaggaatg caataactta aataaatctg tagccatgtc    360
tgtggagcac ggaggaatcc attagggtat aaggtagcaa g                         401

<210> SEQ ID NO 30
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 30
ctctatgaat ttctcatgaa agcattttga gaccagcgtt ttaaagacta ttatttcaaa    60
aacaatgtct gcacaagcca tgaacaaatg ctgaaataag atatttttat tagatgttct   120
tgttgaagca agttggaaca agaagtggta ggaagatatt tatctgtttg cacaaaaaca    180
gtaaactaga tttatttgag naatacattt atcaaaatcc tgttgggagt atatgggttt    240
gggtattcaa aaaatggatg tgagtctctc tgctttccag cctgcctggt caccttcctg    300
cctggagaca gtggtggcta catgtgcatg ttttatatat ctgaatatta gcagtcattt    360
gtcccaatcc cacaagtgct gacaagggtc attgttggag t                         401

<210> SEQ ID NO 31
<211> LENGTH: 401
<212> TYPE: DNA
<213> ORGANISM: Homo sapiens
<220> FEATURE:
```

<221> NAME/KEY: misc_feature
<222> LOCATION: (201)..(201)
<223> OTHER INFORMATION: "n" is C or T.

<400> SEQUENCE: 31

| | | | | |
|---|---|---|---|---|
| acagagtgag | actccgtctc | agaaaaaaaa | aaaaaaaaa | aaagagcaaa | ataaagaaac | 60 |
| agcacttgat | tctctacact | gatcttcaac | agatgtctgg | tttcctttac | ctctgttcca | 120 |
| actgtgatat | actctcataa | taaatctgca | tcttgaattt | aaagttctac | tttcctaaca | 180 |
| gtctgaattt | gcttaagttg | ntgaataata | tgttgaagtt | gtattcatat | ggttagtgaa | 240 |
| agaaaagtag | gttgctggtt | tgtaagccaa | ggggacaaaa | gtgctttctg | ttgatgaacc | 300 |
| gagaaaccaa | tggatataag | gatattataa | ttctctgcaa | ggatattata | attctctgca | 360 |
| gaataagaaa | ttgaagggta | cagtagggaa | ggaagatgaa | t | | 401 |

<210> SEQ ID NO 32
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.

<400> SEQUENCE: 32

| | | | | | | |
|---|---|---|---|---|---|---|
| cagaccaaat | aggaagactt | attttcttgg | gggcattatc | tcacaattcg | aaatagaaga | 60 |
| tttcaaggaa | gaggacctta | aaatattttc | ccaaatcatt | ttgaattagt | ataattccct | 120 |
| ttttttcgaa | aagccctctg | gttaagagta | agagtgttag | aggaataact | caggaaggac | 180 |
| cagaagccaa | tgatctctta | naagtggtca | agccamcaag | tgcttcattg | aagttgggac | 240 |
| tctgggtcaa | ggatttccat | ctgtgaggtc | atatctgttt | cagaataact | tattcaccca | 300 |
| ccagtaactg | acccgaaaaa | ctagagatta | attttttgtca | catttttatt | ggtgtgggga | 360 |
| gcacagagca | atggccaaca | gattgcattc | ttgatagggc | a | | 401 |

<210> SEQ ID NO 33
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 33

| | | | | | | |
|---|---|---|---|---|---|---|
| tgtaagttta | aaagtgcata | caacaactat | agacatttaa | agatatacat | taaatccatt | 60 |
| gaatgttcac | cagcttgggg | tggggaagag | agtaatgaga | gtgggaaata | caatggcata | 120 |
| cacataggta | cgtatttata | aagagggata | ttgcatgggc | taatgatgat | agtaggccat | 180 |
| gaaagttata | taattaactc | nttgttcctg | gaaaataaaa | aatggaagga | aggaattaag | 240 |
| gtgggatgga | agaaaggaag | aaatgcagtg | tgggagggaa | ggaggtttta | ggaaaggaga | 300 |
| aagaaaggaa | aaaaggaagg | agcatgttgc | aaagaagtat | aaagttgcaa | agaagcacag | 360 |
| ataggtatga | ttccatttat | ataaaatttt | gtgtatatat | r | | 401 |

<210> SEQ ID NO 34
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 34
agctctgtgc attacactttt tctcagtctc attatcccat gtcactacct tcctttggag    60
aagagtgcct gtggaggcac agaggaggct ccaagttact tgttacatta ttctaaaaga   120
agcagaaatt cctttttaaac aaraccaggc aggtttgtgt ggggagagag aggatcactc   180
cctaaaatag cattcaaata ngattttttca gaacaattct ggtttctaaa caatcatcgt   240
gatccagaat ctgactmcct gtgcattaca gacttaaaaa ttatgtaaag gatagtattt   300
ggcagtaatt tagaaaacat atttctcaaa gttttctatt tagaccagta ctcctttttct  360 ctaagaataa tgtgagattt tgatcatttg tacagctttc a                       401

<210> SEQ ID NO 35
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 35
acaaacttca gagttgggag ggtctggttg cttaaacaaa ttataggttt ttcaggttaa    60
aaaccatgca agaaatttat cctgtgatcc tgataagggg aaacaatgtg atgttataga   120
tagcatacct acgatcaaat cagtggtgtg tttcatacat ttgtttctta tgaaatgctc   180
aatacaactc tatgacaagg natcacgtag taataagaac acttctacaa aacatcttgg   240
tatgaaactg tcaaatagtt tggtttgatc tagacttcaa tttatagtat ctagggaaat   300
ggatggcttg cacgtcacct catcatcatt cgtaatgatt gctccttgag tctgagcttt   360
tcctgaagga gagcagcaga aagttagagg gaaggggggt t                       401

<210> SEQ ID NO 36
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or C.

<400> SEQUENCE: 36
aggggtgcct ccaggaggag agagaccatg caagaagcag gtgacggggc agtggggkga    60
gcggcccaga gaagcccccc caccccctgg atctcttggg cagtggggcg agtggccagg   120
gaagccccct gtatccccct gggtctcttc tttgagggct tatgctctgt ccgtggtgtg   180
gagccactct tgttcatgca ngttgcagac acaaccactt ttggtccasc aagaatagtt   240
gagctgatca cttgaaagga tcaaaatcca gttgccactg tygaagctyt ggggccacat   300
attttaatat tcctaaattag gcctcaagtt ggatttgttt ttgtgactca aggaaatttt   360
gttctctttc acattctaga attccctgtg aagcagccct g                       401

<210> SEQ ID NO 37
<211> LENGTH: 401
<212> TYPE: DNA
<213> ORGANISM: Homo sapiens
<220> FEATURE:
<221> NAME/KEY: misc_feature
<222> LOCATION: (201)..(201)

<223> OTHER INFORMATION: "n" is C or T.

<400> SEQUENCE: 37

```
aggcagtggt tctccatggg gatgactttg ccttccaggg gacatttggc acggcctgga    60
gacatttcgg gttttcacac tagacaaggg tttccgctgg catgtcgtgg gcagaggcca   120
gagaagctgc taaacatcct ccagtgcaca gggcagcccg tcctccccac aacaaagaat   180
tacctgaccc agaatgtcaa ntgatctaag ttctaaagcc tactkatagt ttgtaagttg   240
aaagcactag attgacacaa acgggaaaag ttatttgcag tttatttttcc tgagggacaa  300
tgggctgcca ctcccttcca tgctattgct gggcaagact ctatgttggc tcttgctttc   360
ttctcctctt tgaacacccc cctcccctgc cagcccgtct g                       401
```

<210> SEQ ID NO 38
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G.

<400> SEQUENCE: 38

```
ttcactggaa tgtctcytag cttctgtttc ttcatccaca aaacagagac gtcaaatcgt    60
acttgcaggt tgtcatgtgg atttgatagg atgatggtga agttggacac atgtctgaca   120
ttctgcaagg gaagcttaat gatgatagac cttagaagaa gtccacaact ctatttcaag   180
ttaaccctcc ccataacttc nttctctctg ctgtgctgaa aggcagtggt tctgaaatgt   240
tgttttagga gagctaaaaa gaaacacaga ggtccgggct cactgacggg tccaggcatc   300
tgcattttc ccaagcgccc tgggtgattc tgacggccag tgcttgggat cctctctaca   360
ggtgaaggtc ccaatcgcaa agctaagaga gagagattct g                       401
```

<210> SEQ ID NO 39
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is C or T.

<400> SEQUENCE: 39

```
tgtgtagttg ttgaggacat ttagggcaac gggccttggg ttgtattctt ctgacccgcc    60
aggcacttgc tgtttgggca tgtcatatac tcttctgagc tttcatttct tcatctgcaa   120
atggggaagt tgagttacag ggtccctcac taacattttg tgattctatg agtttcgaag   180
gccagagaat cagcaagaat ngtattaata agctatcaat gatggtataa aggttttgct   240
tctcactgct gctctttctg ctgtctgatg tgctgggggc actgaggtct atggcaaatg   300
agatcattgg cctggaccat tcacttggcc cttgacagac acaagttggg tctaggattt   360
ctttgcaact atagccaata catacatatt gtagtataat a                       401
```

METHODS TO PREDICT THE OUTCOME OF TREATMENT WITH ANTIDEPRESSANT MEDICATION

CROSS-REFERENCE TO RELATED APPLICATIONS

This patent application claims the benefit of U.S. Provisional Patent Application No. 60/895,649, filed Mar. 19, 2007, which is incorporated by reference.

STATEMENT REGARDING FEDERALLY SPONSORED RESEARCH AND DEVELOPMENT

This invention was made with Government support under Grant N01MH90003 awarded by the National Institutes of Health.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 26,868 Byte ASCII (Text) file named "702696ST25.TXT," created on Mar. 14, 2008.

BACKGROUND OF THE INVENTION

Depression is a disease that affects a large proportion of the population and is a result of multiple factors. According to the World Health Organization (WHO), depression ranks among the ten leading causes of disability and will become the second-largest cause of the global health burden by 2020. An estimated 121 million people worldwide suffer from a depressive disorder for which they require treatment. It is estimated that 5.8% of all men and 9.5% of all women will suffer from a depressive disorder in any given year and that 17% of all men and women will suffer from a depressive disorder at some point in their lives.

Several types of antidepressant medications are used to treat depressive disorders, such as selective serotonin reuptake inhibitors (SSRIs), tricyclics, and monoamine oxidase inhibitors (MAOIs). The SSRIs generally have fewer side effects than tricyclics. Thus SSRIs are the most widely used antidepressants today.

Although the condition of many patients improves with medication, only a minority experience full remission, and patients whose condition responds to one medication may not have a response to others. Individual variation in antidepressant treatment outcome is, at present, unpredictable, but may have a partial genetic basis.

There exists a desire for a method to predict the outcome of treatment with antidepressant medication in individuals.

BRIEF SUMMARY OF THE INVENTION

The invention provides a method for predicting the outcome of treatment with an antidepressant medication in a patient (i.e., whether or not a patient will respond to treatment with an antidepressant medication). The method comprises obtaining a sample of genetic material from the patient, and assaying the sample for the presence of a genotype in the patient which is associated with the outcome of treatment with antidepressant medication, wherein the genotype is characterized by a polymorphism in a gene selected from the group consisting of 5-hydroxytryptamine (serotonin) receptor 2A (HTR2A); glutamine receptor, ionotropic, kainate 4 (GRIK4); B-cell leukemia/lymphoma 2 (BCL2); and a combination thereof.

The invention also provides a method of screening patients to identify those patients with a decreased risk of non-response to treatment with an antidepressant medication. The method comprises obtaining a sample of genetic material from the patients, and assaying the sample for the presence of a genotype in the patients which is associated with a decreased risk of non-response to antidepressant treatment, wherein the genotype is characterized by a polymorphism in a gene selected from the group consisting of HTR2A; GRIK4; BCL2; or a combination thereof.

DETAILED DESCRIPTION OF THE INVENTION

The biological basis for the outcome following treatment with antidepressants, such as SSRIs, previously was unknown. The inventors have determined that specific genetic markers can shed light on the outcome of antidepressant treatment and help to identify the response of individuals to treatment with antidepressant medication. For example, specific polymorphisms in particular genes can be used to identify individuals that are at a decreased risk of non-response to antidepressant treatment, such as citalopram treatment. Individuals without the identified polymorphisms can benefit from closer monitoring, alternative treatments, and/or specialty care.

The inventors utilized the Sequenced Treatment Alternatives to Relieve Depression (STAR*D) trial, which is a large prospective treatment trial for major depression to test whether specific genetic markers could predict the outcome of antidepressant treatment in patients treated with the selective serotonin reuptake inhibitor (SSRI) citalopram.

The inventors identified genetic markers in three genes that correlate with a reduction in absolute risk of having no response to antidepressant treatment. Accordingly, assaying the genotype at these markers can be used to predict the outcome of treatment with antidepressant medication (e.g., a SSRI, such as citalopram). The markers reside in the genes 5-hydroxytryptamine (serotonin) receptor 2A (HTR2A), glutamine receptor, ionotropic, kainate 4 (GRIK4), and B-cell CLL/lymphoma 2 (BCL2).

HTR2A encodes the serotonin 2A receptor, which is down-regulated by citalopram. HTR2A also is known as HTR2 and 5-HT2A receptor. HTR2A is located on chromosome 13q14-q21. HTR2A is identified by GenBank Accession Number NM_000621.

Seven distinct 5-HT receptors have been identified (5-HT1-7). The 5HT2A, B, and C subtypes are positively coupled with the enzyme phospholipase C (PLC). The 5-HT2A receptors are postsynaptic receptors that are highly enriched in neocortex and regulate the function of prefrontal-subcortical circuits. The 5-HT2A receptors interact with Gq/G11 guanine nucleotide binding proteins (G proteins) and thereby stimulate PLC to produce the intracellular second messengers sn-1,2-DAG (an endogenous activator of protein kinase C) and inositol-1,4,5-triphosphate (IP3), which stimulates the release of $Ca^{++}$ from intracellular stores.

GRIK4 encodes a subunit of a kainate glutamate receptor. GRIK4 also is known as KA1, EAA1, and GRIK. GRIK4 is located on chromosome 11q22.3. GRIK4 is identified by GenBank Accession Number NM_014619. GRIK4 encodes a protein that belongs to the glutamate-gated ionic channel family. Glutamate functions as the major excitatory neurotransmitter in the central nervous system through activation of ligand-gated ion channels and G protein-coupled membrane receptors. The protein encoded by GRIK4 forms functional heteromeric kainate-preferring ionic channels with the subunits encoded by related gene family members.

BCL2 encodes a protein involved in cellular development and survival and may be involved in neurogenesis. BCL2 is also known as bcl-2 and resides on chromosome 18q22. BCL2 is identified by GenBank Accession Numbers NM_000633.2 and NM_000657.2.

The invention provides a method of predicting the outcome of treatment with antidepressant medication in a patient comprising (a) obtaining a sample of genetic material from the patient, and (b) assaying the sample for the presence of a genotype in the patient that is associated with outcome to treatment with antidepressant medication, wherein the genotype is characterized by a polymorphism in a gene selected from the group consisting of HTR2A, GRIK4, BCL2, and combinations thereof.

The invention also provides a method of screening patients to identify those patients with a decreased risk of non-response to treatment with antidepressant medication comprising (a) obtaining a sample of genetic material from the patients, and (b) assaying the sample for the presence of a genotype in the patients that is associated with a decreased risk of non-response to treatment with antidepressant medication, wherein the genotype is characterized by a polymorphism in a gene selected from the group consisting of HTR2A, GRIK4, BCL2, and combinations thereof.

A patient refers to an individual awaiting or under medical care and treatment, such as treatment for depression. While the inventive methods are designed for human patients, such methods are applicable to any suitable individual, which includes, but is not limited to, a mammal, such as a mouse, rat, rabbit, hamster, guinea pig, cat, dog, goat, cow, horse, pig, and simian. Human patients include male and female patients of any ethnicity (e.g., Caucasian, Asian, Hispanic, Native American, and Black).

The sample of genetic material can be obtained from the patient by any suitable manner. The sample can be isolated from a source including saliva, buccal cells, hair roots, blood, cord blood, amniotic fluid, interstitial fluid, peritoneal fluid, chorionic villus, semen, or other suitable cell or tissue sample. Methods for isolating genomic DNA from various sources are well-known in the art.

A polymorphism refers to one of multiple alleles of a gene. Preferably, the polymorphism is a single nucleotide polymorphism (SNP).

The polymorphism that is associated with treatment outcome to an antidepressant medication can be any suitable polymorphism. For example, the polymorphism can correlate with a decreased risk of non-response to treatment with antidepressant medication.

The polymorphism can be detected by any suitable manner known in the art. For example, the polymorphism can be detected by techniques, such as allele specific hybridization, allele specific oligonucleotide ligation, primer extension, minisequencing, mass spectroscopy, heteroduplex analysis, single strand conformational polymorphism (SSCP), denaturing gradient gel electrophoresis (DGGE), oligonucleotide microarray analysis, temperature gradient gel electrophoresis (TGGE), and combinations thereof.

The polymorphism that is associated with treatment outcome to antidepressant medication (e.g., that correlates a decreased risk of non-response to treatment with antidepressant medication) in the HTR2A gene typically is within intron 2 or the 3' untranslated region (3' UTR) of HTR2A. In such a situation, intron 2 of HTR2A typically comprises SEQ ID NO: 1 or SEQ ID NO: 2. In the treatment response allele, SEQ ID NO: 1 contains thymine at position 201, rather than cystosine. Similarly, the 3' UTR of HTR2A typically comprises SEQ ID NO: 3.

The markers in HTR2A associated with treatment outcome include rs7997012 (e.g., SEQ ID NO: 1), rs1928040 (e.g., SEQ ID NO: 2), and rs7333412 (e.g., SEQ ID NO: 3). Other markers in HTR2A that correlate with treatment outcome include rs977003 (which identifies a SNP in intron 2 of HTR2A, e.g., SEQ ID NO: 4); rs1745837 (which identifies a SNP in intron 2 of HTR2A, e.g., SEQ ID NO: 5); and rs594242 (which identifies a SNP in intron 2 of HTR2A, e.g., SEQ ID NO: 6).

The polymorphism that is associated with the outcome of treatment with antidepressant medication (e.g., a decreased risk of non-response to treatment with antidepressant medication) in the GRIK4 gene typically is within intron 1 of GRIK4 (GenBank Accession Number NM_000828). In such a situation, intron 1 of GRIK4 typically comprises SEQ ID NO: 7. In the treatment response allele, SEQ ID NO: 7 contains cytosine at position 201, rather than thymine.

The marker in GRIK4 associated with the outcome of treatment with antidepressant medication is rs1954787 (e.g., SEQ ID NO: 7). Other markers in GRIK4 that correlate with treatment outcome include rs6589832 (which identifies a SNP in intron 1 of GRIK4, e.g., SEQ ID NO: 8); rs3133855 (which identifies a SNP in intron 1 of GRIK4, e.g., SEQ ID NO: 9); rs949298 (which identifies a SNP in intron 1 of GRIK4, e.g., SEQ ID NO: 10); rs2156762 (which identifies a SNP in intron 1 of GRIK4, e.g., SEQ ID NO: 11); rs948028 (which identifies a SNP in intron 1 of GRIK4, e.g., SEQ ID NO: 12); rs2186699 (which identifies a SNP in intron 1 of GRIK4, e.g., SEQ ID NO: 13); and rs607800 (which identifies a SNP in the 3' UTR of GRIK4, e.g., SEQ ID NO: 14).

The polymorphism that is associated with the outcome of treatment with antidepressant medication (e.g., that correlates a decreased risk of non-response to treatment with antidepressant medication) is typically in intron 2 of BCL2. In such a situation, intron 2 of BCL2 typically comprises SEQ ID NO: 36. In the treatment response allele, SEQ ID NO: 36 contains cytosine at position 201, rather than adenine.

The markers in BCL2 that correlate with treatment outcome include rs4987825 (which identifies a SNP in intron 2 of BCL2, e.g., SEQ ID NO: 36); rs4941185 (which identifies a SNP in intron 2 of BCL2, e.g., SEQ ID NO: 37); rs1531695 (which identifies a SNP in intron 2 of BCL2, e.g., SEQ ID NO: 38); and rs2850763 (which identifies a SNP in intron 2 of BCL2, e.g., SEQ ID NO: 39).

The invention also comprises assaying for the presence of a genotype that is associated with a decreased risk of non-response to treatment with antidepressant medication, wherein the genotype is characterized by a polymorphism in a gene selected from the group consisting of: glutamate receptor, ionotropic, N-methyl D-aspartate (GRIN) 2A, GRIK2, and combinations thereof. Certain polymorphisms in these genes correlate with treatment response following treatment with the SSRI citalopram.

The polymorphism that is associated with the outcome of treatment with antidepressant medication (e.g., a decreased risk of non-response to treatment with antidepressant medication) in GRIN2A typically is within intron 3 of GRIN2A (GenBank Accession Number NM_000833), which encodes an NMDA-type glutamate receptor subunit. In such a situation, intron 3 of GRIN2A typically comprises SEQ ID NO: 15.

The marker in GRIN2A that is associated with the outcome of treatment with antidepressant medication (e.g., a decreased risk of non-response to treatment with antidepressant medication) is rs6416623 (e.g., SEQ ID NO: 15). Other markers in GRIN2A that correlate with treatment outcome include rs2267795 (which identifies a SNP in intron 5 of GRIN2A, e.g., SEQ ID NO: 16); rs2267796 (which identifies a SNP in intron 5 of GRIN2A, e.g., SEQ ID NO: 17); and rs1448239 (which identifies a SNP in intron 3 of GRIN2A, e.g., SEQ ID NO: 18).

The polymorphism that is associated with the outcome of treatment with antidepressant medication (e.g., a decreased risk of non-response to treatment with antidepressant medication) in GRIK1 typically is within intron 1 of GRIK1 (GenBank Accession Numbers NM_175611 and NM_00830). In such a situation, intron 1 of GRIK1 typically comprises SEQ ID NO: 19.

The marker in GRIK1 that is associated with the outcome of treatment with antidepressant medication (e.g., a decreased risk of non-response to treatment with antidepressant medication) is rs2178865 (e.g., SEQ ID NO: 19). Other markers in GRIK1 that correlate with treatment outcome include rs2832388 (which identifies a SNP in intron 15 of GRIK1, e.g., SEQ ID NO: 20); rs2250863 (which identifies a SNP in intron 8 (GenBank Accession No. NM_175611) or intron 9 (GenBank Accession No. NM_000830) of GRIK1, e.g., SEQ ID NO: 21); rs363429 (which identifies a SNP in intron 7 of GRIK1, e.g., SEQ ID NO: 22); rs2251388 (which identifies a SNP in intron 7 of GRIK1, e.g., SEQ ID NO: 23); rs2832414 (which identifies a SNP in intron 7 of GRIK1, e.g., SEQ ID NO: 24); rs363512 (which identifies a SNP in intron 3 of GRIK1, e.g., SEQ ID NO: 25); rs3787671 (which identifies a SNP in intron 1 of GRIK1, e.g., SEQ ID NO: 26); rs933117 (which identifies a SNP in intron 1 of GRIK1, e.g., SEQ ID NO: 27); rs2178865 (which identifies a SNP in intron 1 of GRIK1, e.g., SEQ ID NO: 28); rs2832438 (which identifies a SNP in intron 1 of GRIK1, e.g., SEQ ID NO: 29); rs2832439 (which identifies a SNP in intron 1 of GRIK1, e.g., SEQ ID NO: 30); rs420121 (which identifies a SNP in intron 1 of GRIK1, e.g., SEQ ID NO: 31); rs2142161 (which identifies a SNP in intron 1 of GRIK1, e.g., SEQ ID NO: 32); rs2248218 (which identifies a SNP in intron 1 of GRIK1, e.g., SEQ ID NO: 33); rs383743 (which identifies a SNP in intron 1 of GRIK1, e.g., SEQ ID NO: 34); and rs2832484 (which identifies a SNP in intron 1 of GRIK1, e.g., SEQ ID NO: 35).

The outcome of treatment with an antidepressant medication refers to whether or not a patient will remit and/or respond to treatment with the antidepressant medication (e.g., an SSRI, such as citalopram). The ability to remit and/or respond to treatment is independent of the tolerability of an individual to the medication.

In individuals that can tolerate the antidepressant medication (i.e., are not allergic to, or report serious side effects with, the antidepressant medication, which would require halting treatment with the antidepressant medication), a non-response refers to a treatment response that does not improve the symptoms associated with depression to a clinically meaningful extent. For example, in the STAR*D trial, non-response to treatment with antidepressant medication refers to patients that achieved less than 40% reduction in baseline 16-item Quick Inventory of Depressive Symptomatology-Clinician-rated (QIDS-$C_{16}$) score at the last treatment visit (Trivedi et al., *Am. J. Psychiatry*, 163: 28-40 (2006); Rush et al., *Control Clin. Trials*, 25: 119-142 (2004); Rush et al., *Biol. Psychiatry*, 54: 573-583 (2003); and Trivedi et al., *Psychol. Med.*, 34: 73-82 (2004)).

Accordingly, patients with a non-response to treatment refers to patients that achieve less than 40% (e.g., less than 35%, less than 30%, less than 25%, less than 20%, less than 15%, less than 10%, or less than 5%) reduction in symptoms of depression following treatment with the antidepressant medication as measured by QIDS-$C_{16}$ score.

Patients that respond positively to treatment with antidepressant medication are patients that achieve at least 50% (e.g., at least 55%, at least 60%, at least 65%, at least 70%, at least 75%, at least 80%, at least 85%, at least 90%, at least 95%, or 100%) reduction in symptoms of depression following treatment with the antidepressant medication as measured by QIDS-$C_{16}$ score.

Positive response to treatment also can be measured by an improvement in one or more symptoms of depression. Such symptoms include emotional and physical symptoms. Examples of emotional symptoms of depression include feelings of guilt, worthlessness, sadness, emptiness, hopelessness, numbness, helplessness, irritability, anxiety, indecisiveness, and/or pessimism, and thoughts of death and suicide. Examples of physical symptoms of depression include headaches, back pain, muscle aches and joint pain, chest pain, digestive problems, exhaustion, fatigue, insomnia, a change in appetite or weight, and dizziness or lightheadedness.

In the STAR*D trial, patients in remission following antidepressant medication refers to patients with a QIDS-$C_{16}$ score of less than or equal to 5 following administration of the antidepressant medication. Therefore, patients that remit following treatment refers to patients that have a QIDS-$C_{16}$ score of less than or equal to 5 (e.g., 5, 4, 3, 2, 1, or 0) following treatment with the antidepressant medication.

Accordingly, the invention also provides a method of identifying patients with an increased likelihood of experiencing remission following treatment with an antidepressant medication comprising (a) obtaining a sample of genetic material from the patients, and (b) assaying the sample for the presence of a genotype in the patients that is associated with an increased likelihood of experiencing remission following treatment with antidepressant medication, wherein the genotype is characterized by a polymorphism in a gene selected from the group consisting of HTR2A, GRIK4, BCL2, and combinations thereof.

The antidepressant medication can be any suitable antidepressant medication known in the art. For example, the antidepressant medication can be a SSRI, a tricyclic antidepressant (TCA), a tetracyclic antidepressant, a MAOI, a reversible inhibitor of monoamine oxidase A (RIMA), a dopamine reuptake inhibitor (DARI), a norepinephrine-dopamine reuptake inhibitor, a norepinephrine reuptake inhibitor (NRI) or (NARI), a serotonin-norepinephrine reuptake inhibitor (SNRI), a selective serotonin reuptake enhancer (SSRE), a noradrenergic and specific serotonergic antidepressant (NaSSA), or another suitable antidepressant medication. Preferably, the antidepressant medication is a SSRI, such as citalopram, alaproclate, escitalopram, etoperidone, fluoxetine, fluvoxamine, paroxetine, sertraline, zimelidine, or combinations thereof.

The invention also provides a kit comprising reagents suitable for applying the methods of the invention. The kit provides the necessary materials for identifying a polymorphism packaged into a suitable container. At a minimum, the kit contains a reagent that identifies a polymorphism in the selected gene that is associated with a selected trait, such as treatment outcome. Preferably, the reagent is a set of primers or a PCR set (a set of primers, DNA polymerase, and 4 nucleoside triphosphates) that hybridizes with the gene or a fragment thereof. The kit also can include other reagents for detecting or measuring the detectable entity and/or a control. Other reagents used for hybridization, prehybridization, DNA extraction, visualization, and the like also can be included.

Sensitivity is the probability that a symptom is present (or the screening test is positive) when a patient has a disorder. The sensitivity of the polymorphism associated with the outcome of treatment with antidepressant medication in the inventive method can be any suitable sensitivity. Preferably, the sensitivity is about 0.5 or higher (e.g., about 0.55, about 0.6, about 0.65, about 0.7, about 0.75, about 0.8, about 0.85, about 0.9, about 0.95, and ranges thereof).

Specificity is the probability that a symptom is not present (or the screening test is negative) when a patient does not have a disorder. The specificity of the polymorphism associated with the outcome of treatment with antidepressant medication in the inventive method can be any suitable specificity. Preferably, the specificity is about 0.5 or higher (e.g., about 0.55, about 0.6, about 0.65, about 0.7, about 0.75, about 0.8, about 0.85, about 0.9, about 0.95, and ranges thereof).

Positive predictive value is the probability that a patient has a disorder given a positive test result. The positive predictive value of the polymorphism associated with the outcome of treatment with antidepressant medication in the inventive method can be any suitable value. Preferably, the positive predictive value is about 0.05 or higher (e.g., about 0.1, about 0.2, about 0.25, about 0.3, about 0.4, about 0.5, about 0.55, about 0.6, about 0.65, about 0.7, about 0.75, about 0.8, about 0.85, about 0.9, about 0.95, and ranges thereof).

Negative predictive value is the probability that a patient has the disorder given a negative test result. The negative predictive value of the polymorphism associated with the outcome of treatment with antidepressant medication in the inventive method can be any suitable value. Preferably, the negative predictive value is about 0.5 or higher (e.g., about 0.55, about 0.6, about 0.65, about 0.7, about 0.75, about 0.8, about 0.85, about 0.9, about 0.95, and ranges thereof).

The following examples further illustrate the invention but, of course, should not be construed as in any way limiting its scope.

EXAMPLE 1

This example demonstrates that genetic markers can be used to identify individuals with a major depressive disorder who have a decreased risk of non-response to treatment with a SSRI, such as citalopram.

Experimental Design

The experimental design and results are essentially as described in McMahon et al. (*Am. J. Hum. Genet.*, 78: 804-814 (2006)). DNA samples were collected from a clinically-representative cohort of 1953 outpatients with major depressive disorder enrolled in the Sequenced Treatment Alternatives to Relieve Depression (STAR*D) trial. Outpatients 18-75 years of age with a baseline Hamilton Depression Rating Scale (see Hamilton et al., *J. Neurol. Neurosurg. Psychiatry*, 23: 56-62 (1960); and Hamilton, *Br. J Soc. Clin. Psychol.*, 6(4): 278-296 (1967)) score of $\geq14$ who met the Diagnostic and Statistical Manual of Mental Disorders (DSM)-IV criteria for non-psychotic major depressive disorder (MDD) were eligible for the trial.

All participants received initial therapy with citalopram, typically starting at 20 mg/day, with dose increases following recommended procedures (see Trivedi et al., *Am. J Psychiatry*, 163(1): 28-40 (2006)). The patients were treated with citalopram under a standard protocol for up to 14 weeks. DNA was extracted from whole blood and genotyped on an Illumina Bead Array platform (see Gunderson et al., *Genome Res.*, 14(5): 870-877 (2004)) for 768 single nucleotide polymorphisms (SNPs) in 68 candidate genes. Genes were selected to sample five broad signaling pathways of potential importance in antidepressant effects: serotonin (20 genes), glutamate (16 genes), dopamine (3 genes), norepinephrine (4 genes), and neurotrophins (4 genes), as well as selected genes in other pathways (21 genes).

The 16-item QIDS-$C_{16}$ score was obtained at baseline at each treatment visit to measure symptom severity. Patients with a baseline QIDS-$C_{16}$ score of greater than 10 were eligible if the treating clinician determined that outpatient treatment with an antidepressant medication was indicated and safe.

Patients were scored for treatment outcome in two ways: designated remission and response. In the absence of external validators, the choice of categorical phenotypes was guided (1) by work with the STAR*D clinicians (in advance of the genotyping) to develop distinctions that had face validity and took advantage of the large body of data available from the STAR*D trial; (2) by ensuring maximal contrast between the outcome groups to improve power, and creating "probable" groups that approximated the more narrowly defined categories to test their robustness; and (3) by paying special attention to full remission of symptoms, since this was the primary target outcome of treatment.

Possible outcomes of the treatment were "remission," defined by a QIDS-$C_{16}$ score of $\leq5$ at the last treatment visit, and "response," defined by a reduction of at least 50% on the QIDS-$C_{16}$ at the last treatment visit. "Non-remission" was defined by a QIDS-$C_{16}$ score of 10-16 at the last treatment visit, and "non-response" was defined by a reduction of less than 40% from the baseline score at the last treatment visit. To avoid misclassification, individuals with a QIDS-$C_{16}$ score of 6-9 at the last treatment visit were excluded from both the "non-remission" and "remission" groups. Similarly, individuals with at least a 40% but less than a 50% reduction were excluded from the "non-response" and "response" groups.

Since failure to consider tolerability could lead to misclassification of intolerant patients as non-responders, all subjects were scored as tolerant, probably tolerant, intolerant, or probably intolerant on the basis of an algorithm that considered study exit data and the Global Rating of Side Effect Burden (GRSEB). In brief, all subjects who elected to continue citalopram at the end of the treatment period were considered tolerant, whereas subjects who refused to continue citalopram or who left the study because of side effects were considered intolerant. The remaining subjects were classified on the basis of GRSEB score into probably tolerant (no more than moderate side effects) or probably intolerant (more than moderate side effects). Subjects who were classified as "intolerant" or "probably intolerant" were removed from the "non-remission" and "non-response" groups, but were retained in the "remission" and "response" groups, since intolerant subjects were probably not able to take the full effective dose of citalopram but might have responded if they had.

Relative change in QIDS-$C_{16}$ score at the last visit (expressed as a percentage change from the initial score) was tested as a quantitative trait, after removal of intolerant and nonadherant subjects.

Exploratory analyses were conducted on alternative sample subsets (e.g., tests in men and women separately and tests in samples from white or black participants only).

Statistical Analysis

The experiment was based on comparison of allele and genotype frequencies between subjects who benefited or did not benefit from citalopram therapy. Because of the number of tests was large, a split sample design was employed. The 1,380 samples genotyped for all SNPs were divided into a "discovery" sample comprising two thirds of the cohort, and a "replication" sample, comprising the remaining third. The two samples were matched for sex and ethnicity ("white," "black," or "other"). Each categorical outcome was tabulated against each marker coded in three ways: presence vs. absence of allele 1, presence vs. absence of allele 2, and the three-valued genotype. For each analysis, Fisher's two-sided exact test (for allele-wise tests only), Pearson chi-square, and the likelihood ratio chi-square tests were considered. These analyses were implemented in the SAS FREQ procedure (SAS Institute Inc., Cary, N.C., USA). Based on power analyses, a p-value of $\leq 0.01$ in the discovery sample and a p-value of $\leq 0.05$ in the replication sample were considered to be a significant association provided that the direction of the association was consistent between the two samples. For the quantitative trait, relative reduction in QIDS-$C_{16}$ and analyses of variance were performed as implemented in the SAS ANOVA procedure (SAS Institute Inc., Cary, N.C., USA).

Receiver operating characteristic (ROC) analyses were carried out using logistic regression implemented in SAS (SAS Institute Inc., Cary, N.C., USA) to examine the effects of markers on the treatment response phenotype. Pair-wise linkage disequilibrium (expressed as $r^2$-value) was calculated using HAPLOVIEW (version 3.2).

Results

Each marker was tested for association with treatment response and remission in the discovery sample. A total of twelve markers met or exceeded the nominal significance level of 0.01 for one or both phenotypes. Of these, marker rs7997012, which resides in the second intron of the gene HTR2A, met or exceeded the nominal significance level of 0.05 in the replication sample for the same allele and phenotype. In HTR2A, significant association was detected, in both discovery and replication samples, between the same allele (e.g., SEQ ID NO: 1) of rs7997012 and treatment response. An additional marker in HTR2A (rs1928040, e.g., SEQ ID NO: 2) showed evidence of association with response and remission in the discovery sample, but not in the replication sample.

On the basis of these results, markers rs7997012 and rs1928040 were genotyped in the remaining subjects and the association with treatment outcome was tested. Significant evidence of association was again observed between marker rs7997012 and treatment outcome with p-values on the order of $10^{-6}$ for the treatment response phenotype.

Since markers rs7997012 and rs1928040 are both intronic SNPs with no known function, two SNPs in HTR2A (markers rs6313 and rs6311, which are located in exons) that may have functional importance were genotyped.

The marker rs7997012 was associated significantly with relative change in initial QIDS-$C_{16}$ score with a p-value of $7.0 \times 10^{-5}$ for allelic and $1.0 \times 10^{-6}$ for genotypic association. Homozygote carriers of the treatment-response-associated marker allele (A allele; reverse strand is T allele) of HTR2A (marker rs7997012) were 16-18% less likely to experience non-response to treatment than homozygote carriers of the G allele (reverse strand is C allele). Association was also observed at other HTR2A SNPs (see Table 1).

TABLE 1

Results of Association Analysis of Genotyped HTR2A Markers, Stratified by Race.

| Phenotype and SNP | ALL P | | | WHITE P | | | BLACK P | | |
|---|---|---|---|---|---|---|---|---|---|
| | N | Allele-wise | Genotype-wise | N | Allele-wise | Genotype-wise | N | Allele-wise | Genotype-wise |
| Remission: | | | | | | | | | |
| rs7997012 | 1,149 | .00024 | .000035 | 911 | .0107 | .0626 | 170 | NS | NS |
| rs1928040 | 1,148 | .0446 | .0701 | 910 | .626 | NS | 170 | NS | NS |
| rs6313 | 1,183 | NS | NS | 942 | NS | NS | 172 | NS | NS |
| rs6311 | 1,180 | NS | NS | 939 | NS | NS | 172 | NS | NS |
| Response: | | | | | | | | | |
| rs7997012 | 1,329 | .000037 | .000002 | 1,049 | .00183 | .000157 | 199 | NS | NS |
| rs1928040 | 1,327 | .0709 | NS | 1,048 | NS | NS | 199 | NS | NS |
| rs6313 | 1,372 | NS | NS | 1,086 | NS | NS | 202 | NS | NS |
| rs6311 | 1,371 | NS | NS | 1,084 | NS | NS | 203 | .0918 | .0149 |
| Change in QIDS-$C_{16}$: | | | | | | | | | |
| rs7997012 | 1,749 | .000007 | .00000146 | 1,380 | .00123 | .000516 | 261 | NS | NS |
| rs1928040 | 1,747 | .0214 | .0072 | 1,387 | .0738 | .0887 | 261 | NS | NS |
| rs6313 | 1,802 | NS | .0878 | 1,425 | NS | NS | 264 | NS | .0353 |
| rs6311 | 1,804 | .0599 | .0494 | 1,426 | NS | NS | 265 | .0094 | .0261 |

NS = not significant

When the sample was divided by race into "white" and "black" strata, the association between HTR2A and treatment outcome was stronger in the white participants. This suggests that genetic variation in HTR2A should be considered along with psychosocial factors in attempts to explain racial differences in antidepressant treatment outcomes.

Genotyping patients at HTR2A markers can help to determine the outcome of treatment with antidepressant medication. For example, genotyping patients at HTR2A markers can identify patients at a decreased risk for non-response to treatment with antidepressant medication. Additionally, absence of the alleles associated with decreased risk for non-response can be used to identify individuals who may suffer from treatment non-response, which patients could benefit from alternative treatment and/or could require closer monitoring. These findings suggest that at least some of that heterogeneity observed in treatment outcome has a genetic basis.

EXAMPLE 2

This example further demonstrates that genetic markers can be used to identify individuals with a major depressive disorder who have a decreased risk of non-response to treatment with a SSRI, such as citalopram.

DNA was collected from the STAR*D consort as set forth in Example 1, except the experiment included 1,816 genotyped samples instead of 1,380 genotyped samples. In addition to the STAR*D DNA samples, control DNAs (N=739) were obtained from individuals that had undergone a basic screening for psychiatric disease. Individuals meeting DSM-IV criteria for major depression or who reported a history of bipolar disorder or psychosis were excluded.

Within the control sample, 105 individuals self-reported as "black." These individuals were excluded from analyses. All remaining individuals in the control sample identified themselves as "white, non-Hispanic." Thus, all comparisons with the STAR*D sample were confined to patients who self-reported "white, non-Hispanic."

Case-control association tests between responders and controls and between non-responders and controls were carried out using the COCAPHASE program from the UNPHASED suite of software, which generates p-values based on a likelihood-ratio test.

In addition to marker rs7997012 in HTR2A, reproducible association was detected between rs1954787 in GRIK4 and both treatment response and remission. This marker is located in the distal end of the first intron of the GRIK4 gene on chromosome 11. Homozygote carriers of the treatment-response-associated marker allele in GRIK4 (marker rs1954787; C allele) had an 11% reduction in non-response.

Several markers in both HTR2A and GRIK4 met or exceeded the nominal significance level for association with treatment response or remission in at least one of the split samples (e.g., discovery sample or replication sample), but only one marker in each gene fulfilled the stringent criteria for significance in both split samples. Homozygote carriers of the treatment-response-associated marker alleles of both GRIK4 (marker rs1954787; C allele) and HTR2A (marker rs7997012; A allele) were 23% less likely to experience non-response to treatment as participants carrying none of these marker alleles. In a separate experiment, the inventors determined that participants with favorable allele combinations in HTR2A, GRIK4, and BCL2 were 50% more likely to remit and 30% more likely to respond to treatment than participants who carried none of the favorable allele combinations.

Since association of a genetic marker with treatment response could reflect an allele that is enriched in frequency in treatment-responders, reduced in frequency in non-responders, or both, allele frequencies of HTR2A and GRIK4 markers in healthy controls were compared with allele frequencies in (1) treatment responders and (2) non-responders. Since all included controls were self-described as "white, non-Hispanic," only STAR*D participants self-described as "white, non-Hispanic" were included in this portion of the experiment. A total of 675 definite responders and 260 definite non-responders were identified, along with 634 healthy controls.

Allele frequency comparisons of sixteen markers in HTR2A revealed significant differences from controls at two markers in responders (rs7997012 and rs594242). Another marker, rs6314, differed significantly in frequency between controls and non-responders.

Allele frequency comparisons of fifty-three markers in GRIK4 revealed twelve markers with significant differences. All were detected in the comparison of controls with non-responders. The most significant difference between non-responders and controls was detected at rs1954787, which was also identified in the comparison of responders and non-responders as described above. The twelve associated markers span an interval of approximately 190 kb in the distal portion of the gene and are not in strong linkage disequilibrium with each other. This suggests that several independent associations were detected, and that common variation in GRIK4 is associated with treatment-resistant depression.

Additional markers were identified that were significant by at least one test in both the discovery and replication samples. Marker rs6416623 showed significant association with treatment response in the analysis of the medication-tolerant as well as the female subsets. Marker rs6416623 resides in the gene GRIN2A, which encodes an NMDA-type glutamate receptor subunit. Marker rs2178865 resides in the gene GRIK1, which encodes a kainic-acid type glutamate receptor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of predicting the outcome of treatment with antidepressant medication in a patient comprising:
   (a) obtaining a sample of genetic material from the patient;
   (b) assaying the sample for the presence of a genotype in the patient which is associated with the outcome of treatment with antidepressant medication; and
   (c) predicting the outcome of treatment with antidepressant medication in the patient based on the presence of the genotype in the sample,
   wherein the genotype is characterized by a polymorphism in a gene having at least one marker, wherein the gene is selected from the group consisting of 5-hydroxytryptamine (serotonin) receptor 2A (HTR2A); glutamine receptor, ionotropic, kainate 4 (GRIK4); B-cell leukemia/lymphoma 2 (BCL2); and a combination thereof, and
   wherein when the selected gene is HTR2A, the polymorphism is located within intron 2 of HTR2A, and the marker is selected from the group consisting of rs7997012, rs1928040, rs7333412, rs977003 and rs1745837, and/or the polymorphism is located within the 3' untranslated region of HTR2A.

2. The method of claim 1, wherein assaying comprises detecting the polymorphism by allele specific hybridization, allele specific oligonucleotide ligation, primer extension, minisequencing, mass spectroscopy, heteroduplex analysis, single strand conformational polymorphism (SSCP), denaturing gradient gel electrophoresis (DGGE), oligonucleotide microarray analysis, temperature gradient gel electrophoresis (TGGE), and combinations thereof.

3. The method of claim 1, wherein the gene is HTR2A.

4. The method of claim 3, wherein the polymorphism is within intron 2 of HTR2A.

5. The method of claim 3, wherein the polymorphism is within the 3' untranslated region of HTR2A.

6. The method of claim 1, wherein the gene is GRIK4.

7. The method of claim 6, wherein the polymorphism is within intron 1 of GRIK4.

8. The method of claim 1, wherein the gene is BCL2.

9. The method of claim 8, wherein the polymorphism is within intron 2 of BCL2.

10. The method of claim 1, wherein the antidepressant medication is a selective serotonin reuptake inhibitor.

11. The method of claim 10, wherein the selective serotonin reuptake inhibitor is citalopram.

12. A method of screening patients to identify those patients with a decreased risk of non-response to treatment with antidepressant medication comprising:
    (a) obtaining a sample of genetic material from the patients;
    (b) assaying the sample for the presence of a genotype in the patients which is associated with a decreased risk of non-response to treatment with antidepressant medication; and
    (c) identifying a decreased risk of non-response to treatment with antidepressant medication in the patients based on the presence of the genotype in the sample,
    wherein the genotype is characterized by a polymorphism in a gene having at least one marker, wherein the gene is selected from the group consisting of 5-hydroxytryptamine (serotonin) receptor 2A (HTR2A); glutamine receptor, ionotropic, kainate 4 (GRIK4); B-cell leukemia/lymphoma 2 (BCL2); and combinations thereof, and
    wherein when the selected gene is HTR2A, the polymorphism is located within intron 2 of HTR2A, and the marker is selected from the group consisting of rs7997012, rs1928040, rs7333412, rs977003 and rs1745837, and/or the polymorphism is located within the 3' untranslated region of HTR2A.

13. The method of claim 12, wherein assaying comprises detecting the polymorphism by allele specific hybridization, allele specific oligonucleotide ligation, primer extension, minisequencing, mass spectroscopy, heteroduplex analysis, single strand conformational polymorphism (SSCP), denaturing gradient gel electrophoresis (DGGE), oligonucleotide microarray analysis, temperature gradient gel electrophoresis (TGGE), and combinations thereof.

14. The method claim 12, wherein the gene is HTR2A.

15. The method of claim 14, wherein the polymorphism is within intron 2 of HTR2A.

16. The method of claim 14, wherein the polymorphism is within the 3' untranslated region of HTR2A.

17. The method of claim 12, wherein the gene is GRIK4.

18. The method of claim 17, wherein the polymorphism is within intron 1 of GRIK4.

19. The method of claim 12, wherein the gene is BCL2.

20. The method of claim 19, wherein the polymorphism is within intron 2 of BCL2.

21. The method of claim 12, wherein assaying for the presence of the genotype comprises detecting the presence of at least one of SEQ ID NOs: 1-18 and 36-39.

22. The method of claim 12, further comprising assaying for the presence of a genotype in the patients which is associated with a decreased risk of non-response to treatment with antidepressant medication, wherein the genotype is characterized by a polymorphism in a gene selected from the group consisting of glutamate receptor, ionotropic, N-methyl D-aspartate (GRIN) 2A; GRIK1; and combinations thereof.

23. The method of claim 22, wherein assaying for the presence of the genotype comprises detecting the presence of at least one of SEQ ID NOs: 19-35.

24. The method of claim 12, wherein the antidepressant medication is a selective serotonin reuptake inhibitor.

25. The method of claim 24, wherein the selective serotonin reuptake inhibitor is citalopram.

* * * * *

UNITED STATES PATENT AND TRADEMARK OFFICE
CERTIFICATE OF CORRECTION

PATENT NO. : 7,795,033 B2  
APPLICATION NO. : 12/051494  
DATED : September 14, 2010  
INVENTOR(S) : McMahon et al.

Page 1 of 1

It is certified that error appears in the above-identified patent and that said Letters Patent is hereby corrected as shown below:

On the title page item (73) which reads:

"Assignees: The United States of America as represented by the Department of Health and Human Services, Washington, DC (US)"

should read:

--The United States of America as represented by the Department of Health and Human Services, Bethesda, MD (US)--

Signed and Sealed this  
Thirty-first Day of May, 2011

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,795,033 B2 | Page 1 of 1 |
| APPLICATION NO. | : 12/051494 | |
| DATED | : September 14, 2010 | |
| INVENTOR(S) | : McMahon et al. | |

It is certified that error appears in the above-identified patent and that said Letters Patent is hereby corrected as shown below:

On the title page item (73) which reads:

"Assignees: The United States of America as represented by the Department of Health and Human Services, Bethesda, MD (US)"

should read:

--The United States of America, as represented by the Secretary, Department of Health and Human Services, Bethesda, MD (US)--

Signed and Sealed this
Twenty-sixth Day of July, 2011

David J. Kappos
*Director of the United States Patent and Trademark Office*